United States Patent [19]

Tocker

[11] Patent Number: 5,441,923
[45] Date of Patent: Aug. 15, 1995

[54] WATER-SOLUBLE OR WATER DISPERSIBLE PESTICIDE GRANULES COMPRISING SULFONYLUREA HERBICIDES IN A POLYETHYLENE OR POLYPROPYLENE COATING

[75] Inventor: Stanley Tocker, Wilmington, Del.

[73] Assignee: E. I. Du Pont de Nemours and Company, Wilmington, Del.

[21] Appl. No.: 195,238

[22] Filed: Feb. 14, 1994

Related U.S. Application Data

[63] Continuation-in-part of Ser. No. 924,632, Aug. 4, 1992, abandoned, which is a continuation of Ser. No. 646,631, Feb. 4, 1991, abandoned, which was filed as PCT/US89/03713, Aug. 13, 1989, which is a continuation of Ser. No. 240,896, Sep. 2, 1988, abandoned.

[51] Int. Cl.$^6$ ............... A01N 25/08; A01N 25/22; A01N 25/26; A01N 47/36
[52] U.S. Cl. ............... 504/125; 504/128; 504/134; 504/136; 504/211; 504/212; 504/213; 504/214; 504/215; 71/DIG. 1
[58] Field of Search ............... 504/212, 211, 213, 214, 504/215, 134, 136; 71/DIG. 1

[56] References Cited

U.S. PATENT DOCUMENTS

| | | | |
|---|---|---|---|
| 3,083,089 | 3/1963 | Renner | 71/2.4 |
| 3,778,248 | 12/1973 | Weston et al. | 71/115 |
| 4,015,970 | 4/1977 | Hennart | 71/11 |
| 4,423,241 | 12/1983 | Caruso | 560/35 |
| 4,921,527 | 5/1990 | Tseng | 71/90 |
| 4,936,901 | 6/1990 | Surgant, Sr. et al. | 71/92 |
| 5,231,071 | 7/1993 | Schumacher et al. | 504/134 |

FOREIGN PATENT DOCUMENTS

| | | |
|---|---|---|
| 528086 | 4/1983 | Australia. |
| 589926 | 12/1959 | Canada. |
| 57-154101 | 9/1981 | Japan. |
| WO87/03579 | 6/1987 | WIPO. |

OTHER PUBLICATIONS

*The Farm Chemicals Handbook*, Charlotte Sine, Ed. Dir., 1987, p. C34.

Primary Examiner—S. Mark Clardy

[57] ABSTRACT

Water-soluble or water-dispersible granular compositions prepared by coating a water-soluble sulfonylurea herbicide or a water-soluble or water-dispersible form of a sulfonylurea herbicide on a granular substrate using a water-soluble polyethylene glycol binder, and a method for controlling undesired vegetation.

10 Claims, No Drawings

WATER-SOLUBLE OR WATER DISPERSIBLE PESTICIDE GRANULES COMPRISING SULFONYLUREA HERBICIDES IN A POLYETHYLENE OR POLYPROPYLENE COATING

CROSS-REFERENCE TO RELATED APPLICATIONS

This is a continuation-in-part of U.S. application Ser. No. 07/924,632 filed Aug. 4, 1992,now abandoned, which is a continuation of U.S. application Ser. No. 07/646,631 filed Feb. 4, 1991, now abandoned, which was filed as PCT/US89/03713, on Aug. 31, 1989, which is a continuation of U.S. Ser. No. 07/240,896, filed Sep. 2, 1988, now abandoned.

BACKGROUND OF THE INVENTION

Sulfonylurea herbicides have proven to be particularly effective herbicides and are in worldwide use. Sulfonylureas are water-sensitive and compositions comprising sulfonylureas can be decomposed in storage by even low residual levels of moisture.

The most common method of applying agricultural pesticides involves their dilution in a solvent followed by spraying of the resulting solution or dispersion. Because of the increasing costs of non-aqueous solvents and the toxicity of some of them, formulations involving water-soluble or water-dispersible granules have become increasingly popular.

Conventional methods for the preparation of water-soluble or water-dispersible granules involve fluidized bed or pan granulation techniques or the impregnation of an active pesticide agent on preformed mineral granules. In the fluidized bed or pan granulation techniques, water is added to the formulation in a granulation step which must then be removed in a drying step. The drying, accomplished by means of a stream of heated air, is expensive because it is energy intensive and requires elaborate dust collection equipment. It would be advantageous to avoid the drying step. Granules prepared by fluidized bed or pan granulation are generally sprayable upon dilution while the impregnated compositions are applied mechanically, for example, using spreaders.

Often it is desirable to use mixtures of two or more pesticides of different functions to provide broad spectrum control over a variety of weeds and/or undesirable organisms, for example a mixture of a herbicide and an insecticide. Unfortunately, some of the individual components are physically or chemically incompatible as mixtures, especially in long-term storage. For example, carbamate insecticides are generally unstable in the presence of alkaline components and sulfonylurea herbicides are known to be unstable in the presence of acidic materials as well as moisture. The chemical incompatibility can be due to an impurity present in the complementary pesticide and not the bioactive component itself. For these reasons it would be desirable to have a sprayable, formulated product consisting of particles or granules wherein the active components are physically separated. Canadian Patent No. 589,926 describes herbicides bonded to a core of prilled fertilizers or inert materials by a water-soluble binder. However, these compositions employ and retain high levels of water and are intended for use in dry form by direct application.

SUMMARY OF THE INVENTION

This invention comprises a water-soluble or water-dispersible, aqueous-sprayable pesticidal granular composition comprising at least one layer coating a substrate, said layer comprising:
  (a) 0.1 to 50% of a water-soluble or water-dispersible sulfonylurea herbicide; and
  (b) 1 to 20% of a solid carrier selected from the class consisting of a water-soluble polyethylene glycol, polypropylene glycol or derivative, copolymer or mixture thereof having a weight average molecular weight in the range of 3000–8000;
the substrate comprising 50 to 98.9% of a water-soluble or water-dispersible granule of a diameter of at least about 500 microns; said foregoing percentages based by weight on the total weight of the layer and the substrate, respectively.

This invention also comprises a process for the preparation of a coated pesticidal granular composition, comprising:
  (a) contacting a water-soluble or water-dispersible granular substrate with a solid polyethylene glycol binder;
  (b) heating the mixture thus obtained to a temperature in the range of 60°–125° C. to at least partially melt the glycol and thereby coat the substrate;
  (c) contacting the coated substrate while the coating is in a molten state with a water-soluble or water-dispersible sulfonylurea herbicide; and
  (d) cooling the resultant coated composition under agitation to solidify the glycol and obtain discrete unagglomerated coated granular particles.

This invention further comprises a method for controlling the growth of undesired vegetation which comprises applying to the locus to be protected, by aqueous spraying, an effective amount of the composition described above.

DETAILED DESCRIPTION OF THE INVENTION

Many pesticides have been formulated to dry flowable granular compositions suitable for coating by the process of this invention. They include herbicidal sulfonamides, phenylether herbicides, glyphosate, metribuzin, bromacil, diuron, hexazinone, manzate, flusizol, oxamyl and hexythiazox. Pesticide (active ingredient) means herbicides, fungicides, insecticides, nematocides, miticides, virucides, algicides, bactericides, plant growth regulants, defoliants, insect attractants and repellents and particularly compatible combinations of the foregoing. A water-soluble pesticide refers to compounds which are substantially dissolved in water under the conditions of temperature and concentration at which application (e.g., spraying of the solution) is to be carried out. A water-dispersible form of a pesticide refers to the various agriculturally suitable formulations including wettable powders used in coatings and dry flowables used as granular substrates. Preferred are herbicides selected from the class of herbicidal sulfonylureas, nonlimiting examples of which include the following. Each of these may be water-soluble or formulated in a water-dispersible or water-soluble form:
  chlorsulfuron
  sulfometuron methyl
  metsulfuron
  tribenuron methyl
  chlorimuron ethyl ethametsulfuron methyl 2-[[(4,6-dimethoxy-1,3,5-triazin-2-yl)aminocarbonyl]aminosulfonyl]-4-(2,2,2-trifluoroethoxy)benzoic acid, ethyl ester 4-chloro-2-[[(4-methoxy-6-methyl-1,3,5-triazin-2-yl)aminocarbonyl]aminosulfonyl]benzoic acid, isopropyl ester thiameturon methyl bensulfuron methyl 2-[[(4,6-dimethoxypyrimidin-2-yl)aminocarbonyl]aminosulfonyl]N,N-dimethyl-3-pyridinecarboxamide 2-[[(4,6-dimethoxypyrimidin-2-yl ))aminocarbonyl]aminosulfonyl]-3-pyridinecarboxylic acid, methyl ester N-[(4,6-dimethoxypyrimidin-2-yl))aminocarbonyl]-3-(ethylsulfonyl)-2-pyridinesulfonamide N-[(4,6-dimethoxypyrimidin-2-yl))aminocarbonyl]-2,3-dihydro-2-methyl-benzo(b)thiophene-7-sulfonamide, 1,1 dioxide 2-[[[[(4,6-bis(difluoromethoxy)-2-pyrimidinyl]amino]carbonyl]amino]sulfonyl]benzoic acid, methyl ester ethyl 5-[3-(4,6-dimethoxypyrimidin-2-yl)ureidosulfonyl]-1-methylpyrazole-4-carboxylate N-[(6-methoxy-4-methyl-1,3,5-triazin-2-yl)aminocarbonyl]-2-(2-chloroethoxy)-benzene sulfonamide N-[(4,6-dimethoxy-1,3,5-triazin-2-yl)aminocarbonyl]-2-(2-methoxyethoxy)-benzenesulfonamide N-[(4,6-dimethoxypyrimidin-2-yl )amino]carbonyl]-3-trifluoromethyl-2-pyridinesulfonamide.

Other types of herbicides that can be advantageously employed in this invention are given below:

acetochlor, acifluorfen, acrolein, alachlor, ametryn, amitrole, ammonium sulfamate (AMS), asulam, atrazine, barban, benerin, bensulide, bentazon, benzofluor, benzoylprop, bifenox, bromacil, bromoxynil, butachlor, buthidazole, butralin, butylate, cacodylic, 2-chloro-N,N-di-2-propenylacetamide (CDAA), 2-chloroallyl diethyldithiocarbamate (CDEC), chloramben, chlorbromuron, chlorimuron, chloroxuron, chlorpropham, chlortoluron, cinmethylin, clethodim, clomazone, cloproxydim, clopyralid, calcium salt of MAA (CMA), cyanazine, cycloate, cycluron, cyperquat, cyprazine, cyprazole, cypromid, dalapon, dazomet, dimethyl 2,3,5,6-tetrachloro-1,4-benzene-dicarboxylate (DCPA), desmediphan, desmetryn, diallate, dicamba, dichlobenil, dichlorprop, dichlofop, diethatyl, difenzoquat, dinitramine, dinoseb, diphenamid, dipropetryn, diquat, diuron, 2-methyl-4,6-dinitrophenol (DNOC), disodium salt of MAA (DSMA), endothall, S-ethyl dipropylcarbamothioate (EPTC), ethalfluralin, ethofumesate, fenac, fenoxaprop, fenuron, fenuron TCA (Salt of fenuron and TCA), flamprop, fluazifop, fluazifop-P, fluchloralin, fluometuron, fluorochloridone, fluorodifen, fluoroglycofen, fluridone, fluroxypyr, fomesafen, fosamine, glypho sate, haloxyfop, hexaflurate, hexazinone, imazamethabenz, imazapyr, imazaquin, imazethapyr, ioxynil, isopropalin, isoproturon, isouron, isoxaben, karbutilate, lactofen, lenacil, linuron, methylarsonic acid (MAA), monoammonium salt of MAA (MAMA), (4-chloro-2-methylphenoxy)acetic acid (MCPA), 4-(4-chloro-2-methylphenoxy)butanoic acid (MCPB), mecoprop, mefluidide, methal-propalin, methabenzthiazuron, metham, methazole, methoxuron, metolachlor, metribuzin, 1,2-dihydro-3,6-pyridazinedione (MH), molinate, monolinuron, monuron, monuron TCA (Salt of monuron and TCA), monosodium salt of MAA (MSMA), napropamide, naptalam, neburon, nitralin, nitrofen, nitrofluorfen, norea, norflurazon, oryzalin, oxadiazon, oxyfluorfen, paraquat, pebulate, pendimethalin, perfluidone, phenmedipham, picloram, 5-[2-chloro-4-(trifluoromethyl)phenoxy]-2-nitroacetophenone oxime-O-acetic acid, methyl ester (PPG-1013), procyazine, profluralin, prometon, prometryn, pronamide, propachlor, propanil, propazine, propham, prosulfalin, prynachlor, pyrazon, quizalofop, secbumeton, sethoxydim, siduron, simazine, sulfometuron, trichloroacetic acid (TCA), tebuthiuron, terbacil, terbuchlor, terbuthylazine, terbutol, terbutryn, thiobencarb, triallate, triclopyr, tridiphane, trifluralin, trimeturon, (2,4-dichlorophenoxy)acetic acid (2,4-D), 4-(2,4-dichlorophenoxy)butanoic acid (2,4-DB), vernolate, xylachlor.

Specifically preferred as coating sulfonylurea herbicides are:

2-[[N(4-methoxy-6-methyl-1,3,5 triazin-2-yl)-N-methylamino]carbonyl]amino]sulfonyl]benzoic acid, methyl ester, 3[[[[(4-methoxy-6-methyl-1,3,5 triazin-2-yl)amino]carbonyl]amino]sulfonyl]-2-thiophene carboxylic acid, methyl ester, methyl 2-[[[[(4,6-dimethoxy-2-pyrimidinyl)amino]carbonyl]amino]sulfonyl]methyl benzoate, methyl-2-[[[[(4-methoxy-6-methyl-1,3,5-triazin-2-yl)amino]carbonyl]amino]sulfonyl]benzoate, 2-chloro-N-[(4-methoxy-6-methyl-1,3,5 -triazin-2-yl )amino]carbonyl]benzenesulfonamide, and their agriculturally suitable salts, and water-dispersible powder formulations of the foregoing. The term "sulfonylurea(s)" as employed in this disclosure include(s) the sulfonylurea, its agriculturally suitable salts, and water-dispersible powder formulations of the foregoing.

Most preferred coating sulfonylurea herbicides are the lithium and sodium salts of 2-[[N-(4-methoxy-6-methyl-1,3,5-triazin-2-yl)-N-methylaminocarbonyl]aminosulfonyl]benzoic acid, methyl ester.

Preferred carriers are water-soluble polyethylene glycols that have a weight average molecular weight between 3000 and 8000. Examples include Carbowax ® polyethylene glycols designated by their weight average molecular weights (Union Carbide Corporation). Derivatives of the water-soluble glycols, e.g., esters and ethers, are also operable. Examples of these include Macol ® DNP150, a monylphenol derivative made by Mazer Chemicals, Inc. and Carbowax ® methoxy polyethylene glycol 5000. Polyethylene glycols having excessively high molecular weights can be impractical due to reduced solution rate.

Preferred is a granular composition wherein the coating sulfonylurea herbicide(s) is (are) embedded in the carrier and the coating sulfonylurea herbicide(s) consist(s) of from 0.5 to 40% of the total weight; the polyethylene glycol, polypropylene glycol, or derivative thereof consists of from 3 to 15% of the total weight, and the substrate consists of 45 to 96.5% of the total weight.

A wide range of materials can be utilized as the granular supporting substrate including prills (e.g., urea, ammonium nitrate), crystals (e.g., sugars) or even water-soluble or water-dispersible granular formulations of other pesticides (e.g., herbicidal sulfonamides, herbicidal phenyl ethers, and herbicidal phosphonomethyl glycine derivatives) or fertilizer. Those materials that are not water-soluble can be used as substrates in granular form or as dry flowables. Specifically preferred granular substrates are potassium carbonate, urea prills, granules of:

2,4-dichlorophenoxyacetic acid,
4-chloro-2-methylphenoxyacetic acid,
(±)- or (R,+)-2-(4-chloro-2-methylphenoxy)propionic acid,
glyphosate,
metribuzin,
methabenzthiazuron, combinations thereof, and their agriculturally suitable salts or solid formulations.

Preferred as substrate classes are dry flowable formulations of herbicidal materials and urea prills. The use of such granular formulations as solid supports thus allows the preparation of water-soluble or water-dispersible granular formulations of otherwise incompatible mixtures of pesticides with the individual components isolated in separate layers. The substrate can comprise a granular pesticide singly or a granular pesticide mixture in combination with the above inert materials or fertilizer, or one or more different pesticides.

When the substrate is a material that produces alkaline solutions, and the pesticide is a herbicidal sulfonamide, the herbicidal sulfonamide can be used in the technical form, and the more water-soluble salt can be generated when the granules are added to water in preparation for spraying. An example of an alkaline substrate is granular potassium carbonate. This improvement eliminates a separate salt promoter.

The carrier can contain more than one active ingredient if the ingredients are not undesirably interactive. Multiple carrier layers can be employed to separate ingredients to prevent undesirable interaction.

The low cost, water-soluble or water-dispersible granular compositions of the present invention are prepared by the layering or coating of a water-soluble sulfonylurea herbicide or preformulated water-dispersible form of a sulfonylurea herbicide onto a granular substrate, itself water-soluble or water-dispersible, using a water-soluble polyethylene glycol as a binder. Preparation of these formulations involves the use of simple mixing techniques and equipment in contrast to the specialized techniques and equipment required for fluidized bed and pan granulation procedures. Even mild agitation allows for the formation of the unagglomerated coated granules of the present invention. The use of simple mixing also allows for the easy incorporation of formulation adjuvants and stabilizers. Preferred among the many known preparation means are mechanical blenders.

In one embodiment, the granular substrate is mixed with the solid polyethylene glycol, or derivative binder and heated to 60°–125° C., preferably 70°–90° C., with constant agitation, until the substrate is coated. "Coated" as used herein means that at least a portion of the substrate is covered. Preferably, the substrate is completely covered. The sulfonylurea herbicide or a mixture of sulfonylurea herbicides in finely divided form is then added to the hot substrate and the blend is slowly cooled to room temperature, all under constant agitation. If a second layer is to be added, additional binder can be added prior to cooling followed by additional sulfonylurea herbicide. Alternatively, the cooled composition can be reheated and a second coating applied as previously described.

If the substrate is a bioactive material or formulated bioactive material, coating of the surface with binder and a sulfonylurea herbicide produces a layered granular product in which the active compounds are physically separated.

Alternatively, a sulfonylurea herbicide or mixture of sulfonylurea herbicides can be preblended with the molten binder and the substrate can be added last.

The present invention further pertains to a method for controlling the growth of undesired vegetation which comprises applying to the locus to be protected, by aqueous spraying, an effective amount of the composition described above. The method of the present invention comprises adding an effective amount of the pesticidal composition to an aqueous medium, forming a solution of the composition, and applying the solution in an effective amount to the locus to be protected, by spraying. The dispersed particles formed on dilution should be no greater than 50 microns, and preferably less than 10 microns, in their largest dimension to avoid nozzle pluggage or premature settling which results in uneven application of the pesticide. Consequently, it is preferred that all of the components of the formulated product rapidly and completely dissolve in the dilution water prior to aqueous spraying. The term "aqueous-sprayable" as employed in this disclosure refers to this ability of the composition to dissolve or disperse in an aqueous solvent and be subsequently sprayed.

EXAMPLE 1

A mixture of 5.0 g of urea prills and 0.3 g of polyethylene glycol of a weight average molecular weight of 8000 (Carbowax ® polyethylene glycol 8000, Union Carbide Corp.) was heated in a steam bath with gentle stirring until the prills were completely coated with polymer. Then 1.0 g of the sodium salt of 2-[[N-(4-methoxy-6-methyl-1,3,5-triazin-2-yl)-N-methyl aminocarbonyl]aminosulfonyl]benzoic acid, methyl ester in powdered form was added with continued stirring and heating. As soon as the prills were evenly coated with the active component, heating was discontinued, and the resultant granules were cooled to room temperature with constant mixing. The product contained 15% of 2-[[N-(4-methoxy-6-methyl 1,3,5-triazin-2-yl)-N-methylaminocarbonyl]aminosulfonyl]benzoic acid, methyl ester. A 1.0 g sample completely dissolved in 100 mL of tap water at 22° C. in 45 seconds with gentle stirring.

EXAMPLE 2

Example 1 was repeated using a mixture of 0.9 g of the lithium salt of 2,4-dichlorophenoxy acetic acid and 0.1 g of the sodium salt of 2-[[N-(4-methoxy-6-methyl-1,3,5-triazin 2-yl)-N-methylaminocarbonyl]aminosulfonyl]benzoic acid, methyl ester, as the active components. The resultant prills completely dissolved in water in 38 seconds under the conditions described in Example 1.

EXAMPLE 3

Example 1 was repeated using 0.9 g of the magnesium salt of a mixture of dichlorprop-P(R)-2-(2,4-dichlorophenoxy)-propionic acid, and 0.1 g of the sodium salt of 2-[[N(4-methoxy-6-methyl-1,3,5-triazin-2-yl)-N-methyl aminocarbonyl]aminosulfonyl]benzoic acid, methyl ester, as the active component. The resultant prills dissolved in under 60 seconds in water.

EXAMPLE 4

Example 1 was repeated using Macol ® DNP 150 (the dinonylphenol derivative of polyethylene glycol, molecular weight (6000, Mazer Chemicals, Inc.) instead of polyethylene glycol. The dissolution time was 55 seconds.

EXAMPLE 5

Urea prills (28.8 g) were heated to 80° C. in a rotating pan and treated portionwise with 4.6 g Carbowax ® 8000. Mixing was continued until all of the prills were coated. Then, 20.5 g of the sodium salt of tribenuron methyl was gradually added while rotation was continued to ensure thorough mixing. This was followed by sequential and gradual addition of 4.0 g more of the Carbowax ® binder and 9.0 g of the sodium salt of tribenuron methyl. The coated prills were then allowed to cool under constant rotation giving a granular product containing 41% tribenuron methyl.

Using the process described in a Example 1, the following granular products were prepared.

| Example Number | Acting Coating | Binder | Granular Substrate |
| --- | --- | --- | --- |
| 6 | tribenuron methyl, sodium salt | PEG 8000 | CaCl$_2$ |
| 7 | tribenuron methyl, sodium salt | PEG 8000 | Sugar |
| 8 | thiameturon methyl, sodium salt + tribenuron methyl, sodium salt (2:1) | PEG 8000 | Urea |
| 9 | thiameturon methyl | PEG 8000 | K$_2$CO$_3$ |
| 10 | tribenuron methyl | PEG 8000 | K$_2$CO$_3$ |
| 11 | thiameturon methyl + tribenuron methyl (2:1) | PEG 8000 | K$_2$CO$_3$ |
| 12 | thiameturon methyl, sodium salt + tribenuron methyl (2:1) | PEG 8000 | K$_2$CO$_3$ |
| 13 | bensulfuron methyl | PEG 8000 | Urea |
| 14 | tribenuron methyl, sodium salt | PEG 8000 | CaCl$_2$ |
| 15 | tribenuron methyl, sodium salt | PEG 8000 | Sugar |

EXAMPLE 16

A mixture of 0.3 g of Carbowax ® polyethylene glycol 8000 and 0.5 g of powdered sodium salt of ethyl-2-[[[[(4-chloro-6-methoxy-2-pyrimidinyl)amino]carbonyl]amino]sulfonyl]benzoate was stirred together under steam bath heating until the powder was wet by the polymer. Then 5.0 g of Lexone ® water dispersible granules (75% metribuzin, manufacturer E. I. du Pont de Nemours and Company) was added and the mixture was stirred while heating until uniform coating was observed. The granules were then cooled to room temperature under constant stirring. The resultant product dispersed in water in under 60 seconds to give a sprayable mixture containing dispersed and dissolved metribuzin along with dissolved sodium salt of ethyl 2-[[[[(4-chloro-6-methoxy-2-pyrimidinyl)amino]carbonyl]amino]sulfonyl]benzoate.

EXAMPLE 17

Example 5 was repeated using herbicide granules as the substrate and 0.6 g of polyethylene glycol 8000 as the binder. The resultant granules are water-dispersible and contain 36% of 2-(2-chlorophenyl)methyl-4,4-dimethyl-3-isooxazolidone.

Using the procedure described in Example 16, the following granular products were prepared:

| EXAMPLE NUMBER | ACTIVE IN COATING | BINDER | DRY-FLOWABLE GRANULAR FORMULATION |
| --- | --- | --- | --- |
| 18 | tribenuron methyl | PEG 8000 | Na salt of 2,4-D, 60% a.i. |
| 19 | thiameturon methyl, lithium salt | PEG 8000 | Na salt of 2,4-D, 60% a.i. |
| 20 | tribenuron methyl | PEG 8000 | Krovar II (bromacil) |

EXAMPLE 21

Example 1 is repeated using 8.0 g of urea prills, 0.54 g of Carbowax ® 8000 and 1.74 g of LONDAX ® containing 60% 2[[[[(4,6-dimethoxy-2-pyrimidinyl)amino]carbonyl]amino]sulfonyl]methylbenzoate and 40% formulation adjuvants. This powder has been used for preparation of uncoated LONDAX ® 60DF, a commercial product used to control weeds in rice. The coated prills, containing 1.0.1% active ingredient, give a fine dispersion of the active ingredient in slightly agitated water approximately 1 min after dilution.

EXAMPLE 22

Example 1 is repeated using 8.6 g of urea prills, 0.28 g of Carbowax ®8000, 1.0 g of the premix powder employed in Example 1 and 0.12 g of sodium hydroxide powder. The resultant prills contain 10.1% active ingredient. Upon addition to slightly agitated water, the product totally dissolves in about 1 min as a result of forming the water soluble salt of the active ingredient in situ by reaction with the sodium hydroxide.

I claim:

1. A water-soluble or water-dispersible, aqueous-sprayable pesticidal granular composition comprising at least one layer coating a substrate, said layer comprising:
    (a) 0.1 to 50% of a water-soluble or water-dispersible sulfonylurea herbicide; and
    (b) 1 to 20% of a solid carrier selected from the class consisting of a water-soluble polyethylene glycol, polypropylene glycol or ester or ether derivative thereof, or a copolymer or mixture thereof having a weight average molecular weight in the range 3000–8000; and the substrate comprising 50 to 98.9% of a water-soluble or water-dispersible granule of a diameter of at least about 500 microns; said foregoing percentages based by weight on the total weight of the layer and the substrate, respectively.

2. The granular composition of claim 1 wherein the sulfonylurea is embedded in the carrier.

3. The composition of claim 1 wherein the percentages of the sulfonylurea, the carrier and the substrate are 0.5 to 40%, 3 to 15% and 45 to 96.5%, respectively.

4. The composition of claim 3 wherein the carrier is polyethylene glycol and the sulfonylurea is a member selected from the class consisting of:

2-[[N-(4-methoxy-6-methyl-1,3,5-triazin-2-yl)-N-methylamino]carbonyl]-amino]sulfonyl]benzoic acid, methyl ester, 3-[[[[(4-methoxy-6-methyl-1,3,5, -triazin-2-yl)amino]-carbonyl]amino]sulfonyl]-2-thiophene carboxylic acid, methyl ester, methyl 2-[[[[(4,6-dimethoxy-2-pyrimidinyl)amino]-carbonyl]amino]sulfonyl]methyl-benzoate methyl-2-[[[[(4-methoxy-6-methyl- 1,3,5-triazin-2-yl)amino]carbonyl]amino]sulfonyl]-benzoate, 2-chloro-N-[(4-methoxy-6-methyl-1,3,5-triazin-1-yl)amino]carbonyl) benzenesulfonamide, and agriculturally suitable salts and water-dispersible formulations of the foregoing.

5. The composition of claim 4 wherein the substrate is a urea prill.

6. The composition of claim 1 wherein the composition comprises multiple layers of carrier embedded with incompatible sulfonylurea herbicides.

7. The composition of claim 1 wherein the substrate comprises a fertilizer.

8. A method for controlling the growth of undesired vegetation which comprises applying to the locus to be protected, by aqueous spraying, an effective amount of the composition of claim 1.

9. The method of claim 8 wherein the substrate comprises a pesticide.

10. The method of claim 8 wherein an effective amount of the composition is added to an aqueous medium to form a solution of the composition for application in an effective amount to the locus to be protected, by spraying; and wherein the substrate comprises a herbicide.

* * * * *